United States Patent [19]

Schwartz

[11] Plant 4,168

[45] Dec. 20, 1977

[54] ROSE PLANT

[75] Inventor: Ernest Schwartz, Kingsville, Md.

[73] Assignee: F. Harmon Saville, Nor'East Miniature Roses, Rowley, Mass.

[21] Appl. No.: 760,918

[22] Filed: Jan. 21, 1977

[51] Int. Cl.[2] ..... A01H 5/00

[52] U.S. Cl. ..... Plt./8

[58] Field of Search ..... Plt./8

*Primary Examiner*—Robert E. Bagwill
*Attorney, Agent, or Firm*—Vincent G. Gioia

[57] ABSTRACT

A novel miniature rose characterized by yellow blooms borne on low, virtually thornless stems.

1 Drawing Figure

1

The present invention relates to a new and distinct variety of rose plant of the miniature rose class, which was originated by my crossing as seed parent a self seedling of the rose known as "Gold Coin" and an unknown seedling as pollen parent.

Among the novel characteristics possessed by this new variety which distinguish it from its parents and all other varieties of which I am aware are: (1) recurrent blooms of persistent yellow coloring, (2) high centered flowers borne primarily singly to a stem in a manner typical of hybrid tea plants, (3) flowers of many petals displaying high centered form, and (4) long lasting blooms on the plant and after cutting which open well under varied weather conditions. Asexual reproduction by budding of the new variety as performed in Essex County, Mass., shows that the foregoing and other distinguishing characteristics come true to form and are established and transmitted through succeeding propagations.

The new and improved rose variety which I have developed is an unusually fine miniature rose of golden yellow coloring, singly-borne blooms of high centered, hybrid-tea like form are delightfully displayed on a small, compact, pin-cushion, shaped plant which tends to be low growing. The flowers are unusually heavily petaled, for a miniature rose with as many as 48 to 52 having been counted. Despite this heavy petalage, the blooms open well and hold their beautiful medium yellow coloring under varied and adverse weather conditions. The plant itself is attractive in combining small, abundant foliage with well branching growth. An especially desirable feature of this new variety is that it has virtually no thorns.

The accompanying drawing shows typical specimens of the vegetative growth and flowers of the new variety in different stages of development and as depicted in color as nearly true as it is reasonably possible to make the same in a color illustration of this character.

The following is detailed description of my new variety, with color terminology in accordance with the Royal Horticultural Society Color Chart (RHSCC). The terminology used in color description herein refers to plate numbers in the aforementioned color chart, e.g., "45B" is plate 45B of the Royal Horticultural Society Color Chart.

Parentage: Seedling.

*Seed parent.*—A self seeding of "Gold Coin".

*Pollen parent.*—"Unknown Seedling".

Class: Miniature.

2

The following observations are made of specimens grown in a greenhouse at Essex County, Mass. during the month of November.

FLOWER

Blooming habit: Continuous.

Bud:

*Size.*—Small.

*Form.*—Ovoid.

*Color.*—When sepals first divide — 150C, yellowish green. When petals begin to unfurl — 11A, yellow. When half-blown: 11A. Reverse side of petals — 10A.

*Sepals.*—Narrow, pointed, extending slightly beyond tip of bud (before opening). *Peduncle.*—Length — ½ to 1-inch. Aspect — straight. Strength — erect. Color — 138B.

Bloom:

*Size.*—Average size when fully expanded — about ½-inch.

*Borne.*—Primarily singly.

*Form.*—High centered blooms, becoming flat upon opening, petals reflexed and pointed, quilling.

*Petalage.*—Number of petals under normal conditions — about 48 to 52, displaying 15 to 20 petaloids.

*Color.*—(during first 2 days).—Inner petals at center of flower — 11A. Outer petals — 11A. Base of petals (point of attachment) — 11A. Reverse of petals — 10B. General tonality from a distance — rich medium yellow near to 10A.

*Color change.*—As bloom ages — holds color until petals drop except for very slight lightening of older petals at edges on aging finishing near to 10D.

Petals:

*Texture.*—Crisp with good substance, thick.

*Appearance.*—Inside — velvety; Outside — satiny, smooth.

*Form.*—Long, pointed, with good quilling.

*Arrangement.*—Regularly arranged, shingle-like.

*Petaloids in center.*—Many, 15 to 20, interspersed with stamens.

*Persistence.*—Drop off cleanly.

*Fragrance.*—Sweet, strong for miniature.

*Lasting quality.*—Very good on plant and as cut flower, holds color well in sun and rain, opens well in all weather conditions.

REPRODUCTIVE ORGANS

Stamens, filaments and anthers:
*Arrangement.*—Irregularly arranged and relatively few.
*Color.*—150D.
Pollen:
*Color.*—Rich yellow near to 12C.
Styles: Bunched, few uneven length.
Stigmans:
*Color.*—23C.
Hips: Rarely sets hips.

PLANT

Form: Small, compact, pin-cushion shape, low growing, close to the ground.
Growth: Very vigorous, considerable branching, almost no candelabra.
Foliage: Mostly 5-leaflet leaves.
*Size.*—Small.
*Quantity.*—Abundant.
*Color.*—New foliage: Upper side — near to 137A. Under side — near to and 138B.
*Shape.*—Pointed, uniformly serrated.
*Texture.*—Smooth, stiff.
*Edge.*—Serrated.
*Serration.*—Uniform.

*Leaf Stem.*—Color — near to 138C on new stems, fading as foliage ages to 137B. Under side — 183B.
*Stipules.*—Long, narrow, smooth.
*Resistance to disease.*—Blackspot — normal. Mildew — normal.
Wood:
*New wood.*—Color — 138C. Bark — smooth.
*Old wood.*—Color — 137C. Bark — smooth.
Thorns:
*Thorns.*—Quantity: few if any on many stalks, none observed on main stalks from base — very few thorns.
*Prickles.*—Few if any — on laterals — none.
Winter hardiness: Good winter hardiness, but needs some mulching because of shallow root system.

I claim:

1. A new and distinct variety of rose plant of the miniature class, substantially as shown and described, characterized particularly by high centered, recurrent flowers of persistent yellow coloring borne primarily singly to a stem, on any petalled flowers which open well under varied weather conditions and are long lasting on the plant and as cut flowers grown on a vigorous but compact growing plant with abundant foliage and virtually no thorns.

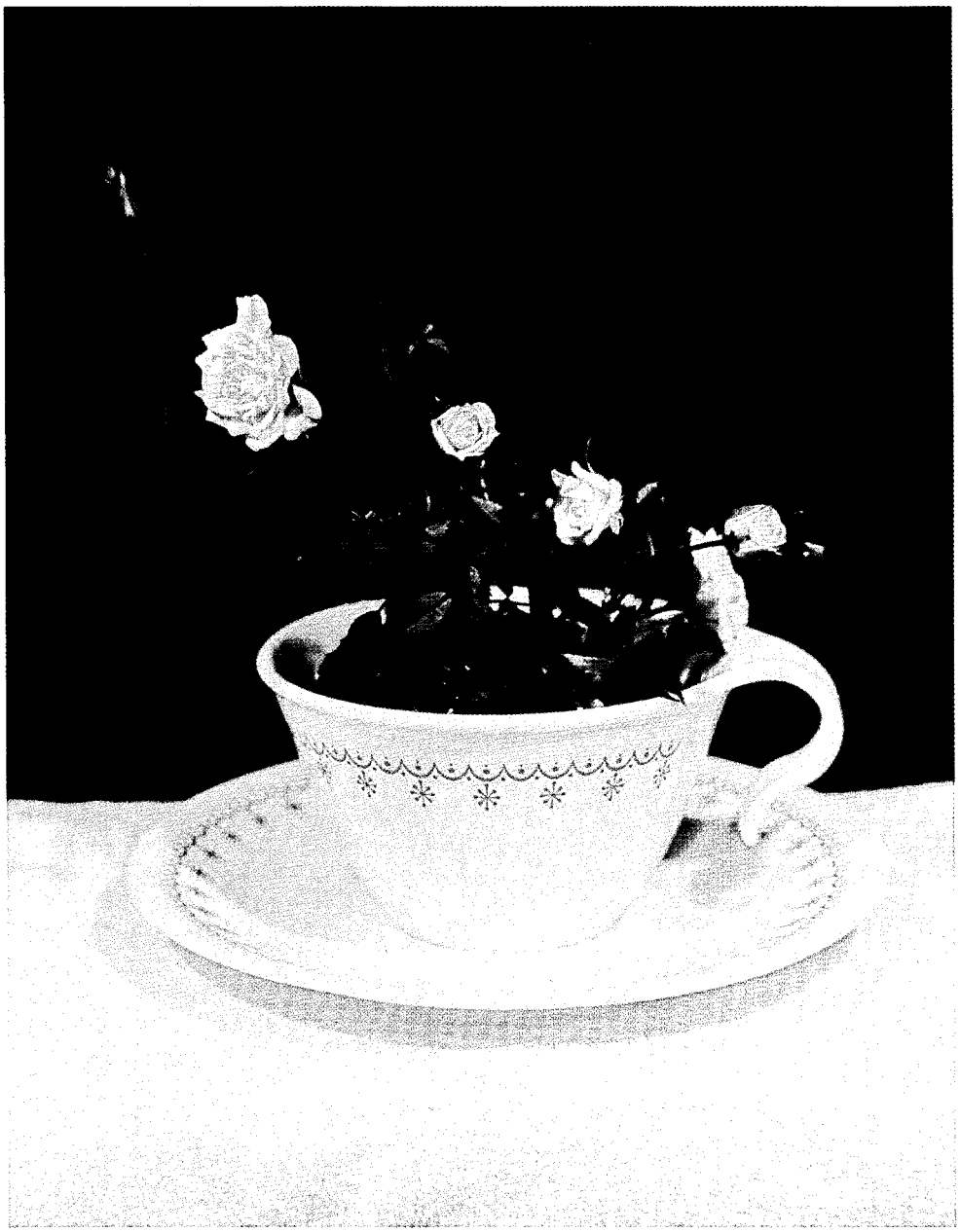

* * * * *